US012637508B2

(12) United States Patent
Verdino et al.

(10) Patent No.: US 12,637,508 B2
(45) Date of Patent: May 26, 2026

(54) ANTIBODIES THAT BIND HUMAN AND MOUSE INSL5 AND ENCODING NUCLEIC ACIDS THEREOF

(71) Applicant: Eli Lilly and Company, Indianapolis, IN (US)

(72) Inventors: Petra Verdino, San Diego, CA (US); Hsiu-Chiung Yang, Smorum (DK)

(73) Assignee: Eli Lilly and Company, Indianapolis, IN (US)

( * ) Notice: Subject to any disclaimer, the term of this patent is extended or adjusted under 35 U.S.C. 154(b) by 660 days.

(21) Appl. No.: 18/006,169

(22) PCT Filed: Aug. 3, 2021

(86) PCT No.: PCT/US2021/044304
§ 371 (c)(1),
(2) Date: Jan. 20, 2023

(87) PCT Pub. No.: WO2022/031674
PCT Pub. Date: Feb. 10, 2022

(65) Prior Publication Data
US 2023/0257460 A1      Aug. 17, 2023

Related U.S. Application Data

(60) Provisional application No. 63/060,701, filed on Aug. 4, 2020.

(51) Int. Cl.
*C07K 16/26*      (2006.01)
*C12N 5/00*      (2006.01)
*C12N 15/85*      (2006.01)

(52) U.S. Cl.
CPC ............... *C07K 16/26* (2013.01); *C12N 5/00* (2013.01); *C12N 15/85* (2013.01); *C07K 2317/21* (2013.01); *C07K 2317/92* (2013.01); *C12N 2800/107* (2013.01)

(58) Field of Classification Search
CPC ............... C07K 16/26; C07K 2317/21; C07K 2317/92; C07K 2317/33; C07K 2317/76; C07K 2317/94; C12N 5/00; C12N 5/85; C12N 2800/107
See application file for complete search history.

(56) References Cited

FOREIGN PATENT DOCUMENTS

WO      2019/157774      8/2019

OTHER PUBLICATIONS

Biocompare.com. "Anti-INSL5 Antibody Products". (https://www.biocompare.com/pfu/110447/soids/23970/Antibodies/INSL5. retrieved from the internet Sep. 2, 2025).*
Office Action, CA Application No. 3,188,429, dated Mar. 20, 2024, 6 pages.
Response to Office Action, CA Application No. 3, 188,429, dated Jul. 19, 2024, 10 pages.
Office Action, CA Application No. 3,188,429, dated May 1, 2025, 5 pages.
Examination Report, AU Application No. 2021322102, dated Nov. 29, 2024, 5 pages.
Response to Examination Report, AU Application No. 2021322102, dated Apr. 29, 2025, 19 pages.
Examination Report, AU Application No. 2021322102, dated May 22, 2025, 2 pages.
Notice of Reasons of Refusal, JP Application No. 2023-507607, dated Apr. 30, 2024, 6 pages.
Response Filed, JP Application No. 2023-507607, dated Aug. 2, 2024, 5 pages.
Decision to Grant, JP Application No. 2023-507607, dated Oct. 21, 2024, 3 pages.
Decision to Grant, JP Application No. 2024-126524, dated Jul. 22, 2025, 3 pages.
Notice of Preliminary Rejection, KR Application No. 10-2023-7006431, dated Aug. 26, 2025, 9 pages.
International Search Report of the International Searching Authority pertaining to International Application No. PCT/US2021/044304; Date of Mailing: Nov. 17, 2021; 7 pages.
Written Opinion of the International Searching Authority pertaining to International Application No. PCT/US2021/044304; Date of Mailing: Nov. 17, 2021; 7 pages.
Anonymous (2018). "ImmunotagTM INSL5 polyclonal antibody", Retrieved from the internet: URL:https://gbiosciences.com/ITN0234 the whole document.
Li, S. B., Liu, Y. Y., Yuan, L., Ji, M. F., Zhang, A., Li, H. Y., . . . & Zeng, M. S. (2020). Autocrine INSL 5 promotes tumor progression and glycolysis via activation of STAT 5 signaling. *EMBO molecular medicine*, 12(9), e12050.

* cited by examiner

*Primary Examiner* — Robert S Landsman
(74) *Attorney, Agent, or Firm* — Nielsen IP Law LLC

(57) ABSTRACT

The present invention provides compounds and methods targeting insulin-like peptide-5 (INSL5), including antibodies, cells and vectors comprising DNA encoding the same, and methods for producing the antibodies. In addition, the present invention provides for use of INSL5 antibodies in diagnostic assays.

20 Claims, No Drawings
Specification includes a Sequence Listing.

SEQUENCE LISTING

<160> NUMBER OF SEQ ID NOS: 29

<210> SEQ ID NO 1
<211> LENGTH: 21
<212> TYPE: PRT
<213> ORGANISM: Homo sapiens

<400> SEQUENCE: 1

Gln Asp Leu Gln Thr Leu Cys Cys Thr Asp Gly Cys Ser Met Thr Asp
1               5                   10                  15

Leu Ser Ala Leu Cys
            20

<210> SEQ ID NO 2
<211> LENGTH: 24
<212> TYPE: PRT
<213> ORGANISM: Homo sapiens

<400> SEQUENCE: 2

Lys Glu Ser Val Arg Leu Cys Gly Leu Glu Tyr Ile Arg Thr Val Ile
1               5                   10                  15

Tyr Ile Cys Ala Ser Ser Arg Trp
            20

<210> SEQ ID NO 3
<211> LENGTH: 21
<212> TYPE: PRT
<213> ORGANISM: Mus musculus

<400> SEQUENCE: 3

Arg Asp Leu Gln Ala Leu Cys Cys Arg Glu Gly Cys Ser Met Lys Glu
1               5                   10                  15

Leu Ser Thr Leu Cys
            20

<210> SEQ ID NO 4
<211> LENGTH: 24
<212> TYPE: PRT
<213> ORGANISM: Mus musculus

<400> SEQUENCE: 4

Arg Gln Thr Val Lys Leu Cys Gly Leu Asp Tyr Val Arg Thr Val Ile
1               5                   10                  15

Tyr Ile Cys Ala Ser Ser Arg Trp
            20

<210> SEQ ID NO 5
<211> LENGTH: 446
<212> TYPE: PRT
<213> ORGANISM: Artificial Sequence
<220> FEATURE:
<223> OTHER INFORMATION: Synthetic Construct

<400> SEQUENCE: 5

Gln Ser Val Glu Glu Ser Gly Gly Arg Leu Val Thr Pro Gly Thr Pro
1               5                   10                  15

Leu Thr Leu Thr Cys Thr Ala Ser Gly Phe Ser Leu Ser Ser Tyr Asp
            20                  25                  30

Met Gly Trp Val Arg Gln Thr Pro Gly Glu Gly Leu Glu Trp Val Gly
        35                  40                  45

Thr Ile Ser Ala Gly Gly Tyr Thr Tyr Tyr Ala His Trp Ala Lys Gly
    50                  55                  60

Arg Phe Thr Ile Ser Lys Ser Ser Thr Thr Val Asp Leu Lys Met Thr
65                  70                  75                  80

Ser Leu Thr Thr Glu Asp Thr Ala Thr Tyr Phe Cys Ala Arg Glu Arg
                85                  90                  95

Trp Asn Tyr Asp Arg Ser Gly Gly Ala Gly Ala Gly Tyr Phe Asp Leu
                100                 105                 110

Trp Gly Pro Gly Thr Leu Val Thr Val Ser Ser Gly Gln Pro Lys Ala
            115                 120                 125

Pro Ser Val Phe Pro Leu Ala Pro Cys Cys Gly Asp Thr Pro Ser Ser
        130                 135                 140

Thr Val Thr Leu Gly Cys Leu Val Lys Gly Tyr Leu Pro Glu Pro Val
145                 150                 155                 160

Thr Val Thr Trp Asn Ser Gly Thr Leu Thr Asn Gly Val Arg Thr Phe
                165                 170                 175

Pro Ser Val Arg Gln Ser Ser Gly Leu Tyr Ser Leu Ser Ser Val Val
                180                 185                 190

Ser Val Thr Ser Ser Ser Gln Pro Val Thr Cys Asn Val Ala His Pro
            195                 200                 205

Ala Thr Asn Thr Lys Val Asp Lys Thr Val Ala Pro Ser Thr Cys Ser
    210                 215                 220

Lys Pro Thr Cys Pro Pro Pro Glu Leu Leu Gly Gly Pro Ser Val Phe
225                 230                 235                 240

Ile Phe Pro Pro Lys Pro Lys Asp Thr Leu Met Ile Ser Arg Thr Pro
                245                 250                 255

Glu Val Thr Cys Val Val Val Asp Val Ser Gln Asp Asp Pro Glu Val
                260                 265                 270

Gln Phe Thr Trp Tyr Ile Asn Asn Glu Gln Val Arg Thr Ala Arg Pro
            275                 280                 285

Pro Leu Arg Glu Gln Gln Phe Asn Ser Thr Ile Arg Val Val Ser Thr
    290                 295                 300

Leu Pro Ile Thr His Gln Asp Trp Leu Arg Gly Lys Glu Phe Lys Cys
305                 310                 315                 320

Lys Val His Asn Lys Ala Leu Pro Ala Pro Ile Glu Lys Thr Ile Ser
                325                 330                 335

Lys Ala Arg Gly Gln Pro Leu Glu Pro Lys Val Tyr Thr Met Gly Pro
            340                 345                 350

Pro Arg Glu Glu Leu Ser Ser Arg Ser Val Ser Leu Thr Cys Met Ile
            355                 360                 365

Asn Gly Phe Tyr Pro Ser Asp Ile Ser Val Glu Trp Glu Lys Asn Gly
    370                 375                 380

Lys Ala Glu Asp Asn Tyr Lys Thr Thr Pro Ala Val Leu Asp Ser Asp
385                 390                 395                 400

Gly Ser Tyr Phe Leu Tyr Asn Lys Leu Ser Val Pro Thr Ser Glu Trp
            405                 410                 415

Gln Arg Gly Asp Val Phe Thr Cys Ser Val Met His Glu Ala Leu His
            420                 425                 430

Asn His Tyr Thr Gln Lys Ser Ile Ser Arg Ser Pro Gly Lys
            435                 440                 445

<210> SEQ ID NO 6
<211> LENGTH: 1338
<212> TYPE: DNA
<213> ORGANISM: Artificial Sequence
<220> FEATURE:
<223> OTHER INFORMATION: Synthetic Construct

<400> SEQUENCE: 6
cagtcggtgg aggagtccgg gggtcgcctg gtcacgcctg ggacacccct gacactcacc      60
tgcacagcct ctggattctc cctcagtagc tacgacatgg gctgggtccg ccagactcca     120
ggggaggggc tggaatgggt cggaaccatt agtgctggtg gttacacgta ctacgcgcac     180
tgggcgaaag gccgattcac catctccaaa tcctcgacca cggtggatct gaaaatgacc     240
agtctgacga ccgaggacac ggccacctat ttctgtgcca gagaaagatg gaattacgat     300
aggtctggtg gtgctggtgc tggctacttt gacttgtggg gccaggcac cctggtcacc     360 gtctcctcag ggcaacctaa ggctccatca gtctttcccc tcgcaccttg ctgtggtgac     420
acgccctcat ccacggtaac actgggctgt cttgtcaaag ataccttcc ggagccagtc     480 acagtaacgt ggaactcggg aacattgaca aacggcgtaa gaacgtttcc gtcggtacgt     540
caaagttcag gcctctactc gctcagctcc gtagtatcgg tgacctcatc agccagccg     600 gtgacttgca acgtggcgca tcccgcgacc aacacaaaag tggataagac cgttgcaccc     660
tcaacttgct ccaagcccac gtgtcccca ccagagctgc tcggtgggcc ctcggtcttt     720
atcttccctc cgaaacccaa agacacattg atgatctctc gcacgccgga agtcacgtgc     780
gtggtcgtgg acgtcagcca agatgacccg gaagtgcaat tcacctggta tatcaataac     840
gaacaggtca gaacggctcg gcctcctttg cgagaacaac agttcaattc cactatcagg     900
gttgtatcaa cacttcccat cacacaccaa gattggctta ggggaaagga gtttaagtgt     960
aaagtgcaca ataaggcttt gccagcgcct attgagaaaa ccatttccaa agcccgtggg    1020
caaccgcttg aacccaaagt ctatacaatg gggccaccca gagaggaact gtcgagccgc    1080
tccgtgtcac tgacttgtat gatcaatggg ttctatccgt cggacatttc ggtggaatgg    1140
gagaagaatg gaaaagcaga ggataactac aaaactacgc cagccgtgtt ggactctgac    1200
gggtcatact ttctgtacaa taagctctct gtccccacgt cggaatggca gaggggagat    1260
gtgtttactt gctcggtgat gcatgaggcg ctccataatc actatcccca gaaaagcatc    1320
agtcgaagcc ctgggaaa                                                  1338

<210> SEQ ID NO 7
<211> LENGTH: 216
<212> TYPE: PRT
<213> ORGANISM: Artificial Sequence
<220> FEATURE:
<223> OTHER INFORMATION: Synthetic Construct

<400> SEQUENCE: 7

Ala Asp Val Val Met Thr Gln Thr Ala Ser Pro Val Ser Ala Ala Val
1               5                   10                  15

Gly Gly Thr Val Thr Ile Asn Cys Gln Ala Ser Gln Ser Ile Thr Ser
            20                  25                  30

-continued

```
Ser Tyr Leu Ser Trp Tyr Gln Gln Lys Pro Gly Gln Pro Pro Lys Leu
        35                  40                  45

Leu Ile Tyr Pro Ala Ala Asn Leu Ala Ser Gly Val Pro Ser Arg Phe
        50                  55                  60

Lys Gly Ser Gly Ser Gly Thr Gln Phe Thr Leu Thr Ile Ser Gly Val
65                  70                  75                  80

Gln Cys Asp Asp Ala Ala Thr Tyr Tyr Cys Leu Tyr Gly Tyr Phe Ser
                85                  90                  95

Ser Ser Ile Asp Phe Ala Phe Gly Gly Gly Thr Glu Val Val Val Arg
                100                 105                 110

Gly Asp Pro Val Ala Pro Thr Val Leu Ile Phe Pro Pro Ala Ala Asp
            115                 120                 125

Gln Val Ala Thr Gly Thr Val Thr Ile Val Cys Val Ala Asn Lys Tyr
        130                 135                 140

Phe Pro Asp Val Thr Val Thr Trp Glu Val Asp Gly Thr Thr Gln Thr
145                 150                 155                 160

Thr Gly Ile Glu Asn Ser Lys Thr Pro Gln Asn Ser Ala Asp Cys Thr
                165                 170                 175

Tyr Asn Leu Ser Ser Thr Leu Thr Leu Thr Ser Thr Gln Tyr Asn Ser
                180                 185                 190

His Lys Glu Tyr Thr Cys Lys Val Thr Gln Gly Thr Thr Ser Val Val
            195                 200                 205

Gln Ser Phe Asn Arg Gly Asp Cys
        210                 215

<210> SEQ ID NO 8
<211> LENGTH: 648
<212> TYPE: DNA
<213> ORGANISM: Artificial Sequence
<220> FEATURE:
<223> OTHER INFORMATION: Synthetic Construct

<400> SEQUENCE: 8
gccgatgtcg tgatgaccca gactgcatcc cccgtgtctg cagctgtggg aggcacagtc      60
accatcaatt gccaggccag tcagagtatt actagtagct acttatcctg gtatcagcag     120
aaaccagggc agcctcccaa gctcctgatc tatcctgcag ccaatctggc atctggagtc     180
ccatcgcggt tcaaaggcag tggatctggg acacagttca ctctcaccat cagcggcgtg     240
cagtgtgacg atgctgccac ttactactgt ctatacggtt attttagttc tagtattgat     300
tttgctttcg gcggagggac cgaggtggtg gtcagaggtg atccagttgc acctactgtc     360
ctcatcttcc caccagctgc tgatcaagtc gcaacaggta ctgtgacgat cgtgtgtgtc     420
gcgaacaaat actttcccga cgtgaccgtg acgtgggaag tcgacggaac aacccagacg     480
accgggatcg aaaactcaaa gacccccgcaa aactcggccg attgcacata caatttgtcc     540
tctacgctta cactcacgtc gacgcagtac aatagtcaca aggagtatac atgcaaagtt     600
actcaaggaa ctacgagcgt ggtccagtca ttcaatagag gggattgt                   648

<210> SEQ ID NO 9
<211> LENGTH: 123
<212> TYPE: PRT
<213> ORGANISM: Artificial Sequence
<220> FEATURE:
<223> OTHER INFORMATION: Synthetic Construct

<400> SEQUENCE: 9

Gln Ser Val Glu Glu Ser Gly Gly Arg Leu Val Thr Pro Gly Thr Pro
```

-continued

```
1               5                    10                   15

Leu Thr Leu Thr Cys Thr Ala Ser Gly Phe Ser Leu Ser Ser Tyr Asp
            20                   25                   30

Met Gly Trp Val Arg Gln Thr Pro Gly Glu Gly Leu Glu Trp Val Gly
            35                   40                   45

Thr Ile Ser Ala Gly Gly Tyr Thr Tyr Tyr Ala His Trp Ala Lys Gly
        50                   55                   60

Arg Phe Thr Ile Ser Lys Ser Ser Thr Thr Val Asp Leu Lys Met Thr
65                   70                   75                   80

Ser Leu Thr Thr Glu Asp Thr Ala Thr Tyr Phe Cys Ala Arg Glu Arg
                85                   90                   95

Trp Asn Tyr Asp Arg Ser Gly Gly Ala Gly Ala Gly Tyr Phe Asp Leu
            100                  105                  110

Trp Gly Pro Gly Thr Leu Val Thr Val Ser Ser
        115                  120
```

<210> SEQ ID NO 10
<211> LENGTH: 13
<212> TYPE: PRT
<213> ORGANISM: Artificial Sequence
<220> FEATURE:
<223> OTHER INFORMATION: Synthetic Construct

<400> SEQUENCE: 10

```
Thr Ala Ser Gly Phe Ser Leu Ser Ser Tyr Asp Met Gly
1               5                    10
```

<210> SEQ ID NO 11
<211> LENGTH: 9
<212> TYPE: PRT
<213> ORGANISM: Artificial Sequence
<220> FEATURE:
<223> OTHER INFORMATION: Synthetic Construct

<400> SEQUENCE: 11

```
Thr Ile Ser Ala Gly Gly Tyr Thr Tyr
1               5
```

<210> SEQ ID NO 12
<211> LENGTH: 20
<212> TYPE: PRT
<213> ORGANISM: Artificial Sequence
<220> FEATURE:
<223> OTHER INFORMATION: Synthetic Construct

<400> SEQUENCE: 12

```
Ala Arg Glu Arg Trp Asn Tyr Asp Arg Ser Gly Gly Ala Gly Ala Gly
1               5                    10                   15

Tyr Phe Asp Leu
            20
```

<210> SEQ ID NO 13
<211> LENGTH: 112
<212> TYPE: PRT
<213> ORGANISM: Artificial Sequence
<220> FEATURE:
<223> OTHER INFORMATION: Synthetic Construct

<400> SEQUENCE: 13

```
Ala Asp Val Val Met Thr Gln Thr Ala Ser Pro Val Ser Ala Ala Val
1               5                    10                   15

Gly Gly Thr Val Thr Ile Asn Cys Gln Ala Ser Gln Ser Ile Thr Ser
```

-continued

```
                 20                    25                    30

Ser Tyr Leu Ser Trp Tyr Gln Gln Lys Pro Gly Gln Pro Pro Lys Leu
        35                    40                    45

Leu Ile Tyr Pro Ala Ala Asn Leu Ala Ser Gly Val Pro Ser Arg Phe
    50                    55                    60

Lys Gly Ser Gly Ser Gly Thr Gln Phe Thr Leu Thr Ile Ser Gly Val
65                    70                    75                    80

Gln Cys Asp Asp Ala Ala Thr Tyr Tyr Cys Leu Tyr Gly Tyr Phe Ser
                85                    90                    95

Ser Ser Ile Asp Phe Ala Phe Gly Gly Gly Thr Glu Val Val Val Arg
            100                   105                   110

<210> SEQ ID NO 14
<211> LENGTH: 12
<212> TYPE: PRT
<213> ORGANISM: Artificial Sequence
<220> FEATURE:
<223> OTHER INFORMATION: Synthetic Construct

<400> SEQUENCE: 14

Gln Ala Ser Gln Ser Ile Thr Ser Ser Tyr Leu Ser
1               5                   10

<210> SEQ ID NO 15
<211> LENGTH: 8
<212> TYPE: PRT
<213> ORGANISM: Artificial Sequence
<220> FEATURE:
<223> OTHER INFORMATION: Synthetic Construct

<400> SEQUENCE: 15

Tyr Pro Ala Ala Asn Leu Ala Ser
1               5

<210> SEQ ID NO 16
<211> LENGTH: 12
<212> TYPE: PRT
<213> ORGANISM: Artificial Sequence
<220> FEATURE:
<223> OTHER INFORMATION: Synthetic Construct

<400> SEQUENCE: 16

Leu Tyr Gly Tyr Phe Ser Ser Ser Ile Asp Phe Ala
1               5                   10

<210> SEQ ID NO 17
<211> LENGTH: 435
<212> TYPE: PRT
<213> ORGANISM: Artificial Sequence
<220> FEATURE:
<223> OTHER INFORMATION: Synthetic Construct

<400> SEQUENCE: 17

Gln Ser Val Glu Glu Ser Gly Gly Gly Leu Val Thr Pro Gly Gly Ser
1               5                   10                  15

Leu Thr Leu Thr Cys Thr Val Ser Gly Ile Asp Leu Thr Thr Tyr Ala
            20                    25                    30

Met Gly Trp Val Arg Gln Ala Pro Gly Glu Gly Leu Glu Trp Ile Gly
        35                    40                    45

Ile Ile Gly Gly Gly Gly Arg Thr Tyr Tyr Ala Ala Trp Ala Lys Gly
    50                    55                    60

Arg Phe Thr Ile Ser Lys Thr Ser Thr Thr Val Asp Leu Arg Ile Thr
```

-continued

```
65                 70                 75                 80

Ser Pro Ala Thr Glu Asp Thr Ala Thr Tyr Phe Cys Val Arg Gly Gly
                85                 90                 95

Asp Phe Phe Asp Leu Trp Gly Pro Gly Thr Leu Val Thr Val Ser Ser
                100                105                110

Gly Gln Pro Lys Ala Pro Ser Val Phe Pro Leu Ala Pro Cys Cys Gly
            115                120                125

Asp Thr Pro Ser Ser Thr Val Thr Leu Gly Cys Leu Val Lys Gly Tyr
    130                135                140

Leu Pro Glu Pro Val Thr Val Thr Trp Asn Ser Gly Thr Leu Thr Asn
145                150                155                160

Gly Val Arg Thr Phe Pro Ser Val Arg Gln Ser Ser Gly Leu Tyr Ser
                165                170                175

Leu Ser Ser Val Val Ser Val Thr Ser Ser Ser Gln Pro Val Thr Cys
                180                185                190

Asn Val Ala His Pro Ala Thr Asn Thr Lys Val Asp Lys Thr Val Ala
            195                200                205

Pro Ser Thr Cys Ser Lys Pro Thr Cys Pro Pro Glu Leu Leu Gly
    210                215                220

Gly Pro Ser Val Phe Ile Phe Pro Pro Lys Pro Lys Asp Thr Leu Met
225                230                235                240

Ile Ser Arg Thr Pro Glu Val Thr Cys Val Val Val Asp Val Ser Gln
                245                250                255

Asp Asp Pro Glu Val Gln Phe Thr Trp Tyr Ile Asn Asn Glu Gln Val
                260                265                270

Arg Thr Ala Arg Pro Pro Leu Arg Glu Gln Gln Phe Asn Ser Thr Ile
            275                280                285

Arg Val Val Ser Thr Leu Pro Ile Thr His Gln Asp Trp Leu Arg Gly
    290                295                300

Lys Glu Phe Lys Cys Lys Val His Asn Lys Ala Leu Pro Ala Pro Ile
305                310                315                320

Glu Lys Thr Ile Ser Lys Ala Arg Gly Gln Pro Leu Glu Pro Lys Val
                325                330                335

Tyr Thr Met Gly Pro Pro Arg Glu Glu Leu Ser Ser Arg Ser Val Ser
                340                345                350

Leu Thr Cys Met Ile Asn Gly Phe Tyr Pro Ser Asp Ile Ser Val Glu
            355                360                365

Trp Glu Lys Asn Gly Lys Ala Glu Asp Asn Tyr Lys Thr Thr Pro Ala
    370                375                380

Val Leu Asp Ser Asp Gly Ser Tyr Phe Leu Tyr Asn Lys Leu Ser Val
385                390                395                400

Pro Thr Ser Glu Trp Gln Arg Gly Asp Val Phe Thr Cys Ser Val Met
                405                410                415

His Glu Ala Leu His Asn His Tyr Thr Gln Lys Ser Ile Ser Arg Ser
            420                425                430

Pro Gly Lys
        435
```

<210> SEQ ID NO 18
<211> LENGTH: 1305
<212> TYPE: DNA
<213> ORGANISM: Artificial Sequence
<220> FEATURE:
<223> OTHER INFORMATION: Synthetic Construct -continued

```
<400> SEQUENCE: 18
cagtcggtgg aggagtccgg aggaggcctg gtaacgcctg gaggatccct gacactcacc      60
tgcacagtct ctggaatcga cctcactacc tatgcaatgg gctgggtccg ccaggctcca     120
ggggaggggc tggaatggat cggaattatt ggtggtggtg gtcgaacata ctacgcggcc     180
tgggcgaaag gccgcttcac catctccaaa acctcgacca cggtggatct gagaatcacc     240
agtccggcaa ccgaggacac ggccacctat ttctgtgtca gaggaggaga cttctttgac     300
ttgtggggcc caggcaccct ggtcaccgtc tcctcagggc aacctaaggc tccatcagtc     360
tttcccctcg caccttgctg tggtgacacg ccctcatcca cggtaacact gggctgtctt     420
gtcaaaggat accttccgga gccagtcaca gtaacgtgga actcgggaac attgacaaac     480
ggcgtaagaa cgtttccgtc ggtacgtcaa agttcaggcc tctactcgct cagtccgta      540 gtatcggtga cctcatccag ccagccggtg acttgcaacg tggcgcatcc cgcgaccaac     600
acaaaagtgg ataagaccgt tgcaccctca acttgctcca gcccacgtg tcccccacca      660 gagctgctcg gtgggccctc ggtctttatc ttccctccga aacccaaaga cacattgatg     720
atctctcgca cgccggaagt cacgtgcgtg gtcgtggacg tcagccaaga tgacccggaa     780
gtgcaattca cctggtatat caataacgaa caggtcagaa cggctcggcc tcctttgcga     840
gaacaacagt tcaattccac tatcagggtt gtatcaacac ttcccatcac acaccaagat     900
tggcttaggg gaaaggagtt taagtgtaaa gtgcacaata aggctttgcc agcgcctatt     960
gagaaaacca tttccaaagc ccgtgggcaa ccgcttgaac ccaaagtcta tacaatgggg    1020
ccacccagag aggaactgtc gagccgctcc gtgtcactga cttgtatgat caatgggttc    1080
tatccgtcgg acatttcggt ggaatgggag aagaatggaa aagcagagga taactacaaa    1140
actacgccag ccgtgttgga ctctgacggg tcatactttc tgtacaataa gctctctgtc    1200
cccacgtcgg aatggcagag gggagatgtg tttacttgct cggtgatgca tgaggcgctc    1260
cataatcact atacccagaa aagcatcagt cgaagccctg ggaaa                    1305

<210> SEQ ID NO 19
<211> LENGTH: 214
<212> TYPE: PRT
<213> ORGANISM: Artificial Sequence
<220> FEATURE:
<223> OTHER INFORMATION: Synthetic Construct

<400> SEQUENCE: 19

Ala Gln Val Leu Thr Gln Thr Pro Ala Ser Val Ser Ala Ala Val Gly
1               5                   10                  15

Gly Thr Val Thr Ile Lys Cys Gln Ala Ser Glu Asp Ile Ser Lys Tyr
                20                  25                  30

Leu Ser Trp Tyr Gln Gln Lys Pro Gly Gln Arg Pro Lys Leu Leu Ile
            35                  40                  45

Tyr Tyr Val Ser Asn Leu Glu Phe Gly Val Pro Ser Arg Phe Lys Gly
        50                  55                  60

Ser Gly Ser Gly Thr Glu Tyr Thr Leu Thr Ile Ser Asp Leu Glu Cys
65                  70                  75                  80

Asp Asp Ala Ala Thr Tyr Tyr Cys His Gln Gly Tyr Thr Gly Val Asn
                85                  90                  95

Val Glu Asn Val Phe Gly Gly Gly Thr Glu Val Val Val Arg Gly Asp
            100                 105                 110

Pro Val Ala Pro Thr Val Leu Ile Phe Pro Pro Ala Ala Asp Gln Val
        115                 120                 125
```

-continued

```
Ala Thr Gly Thr Val Thr Ile Val Cys Val Ala Asn Lys Tyr Phe Pro
    130                 135                 140

Asp Val Thr Val Thr Trp Glu Val Asp Gly Thr Thr Gln Thr Thr Gly
145                 150                 155                 160

Ile Glu Asn Ser Lys Thr Pro Gln Asn Ser Ala Asp Cys Thr Tyr Asn
                165                 170                 175

Leu Ser Ser Thr Leu Thr Leu Thr Ser Thr Gln Tyr Asn Ser His Lys
            180                 185                 190

Glu Tyr Thr Cys Lys Val Thr Gln Gly Thr Thr Ser Val Val Gln Ser
            195                 200                 205

Phe Asn Arg Gly Asp Cys
    210
```

```
<210> SEQ ID NO 20
<211> LENGTH: 642
<212> TYPE: DNA
<213> ORGANISM: Artificial Sequence
<220> FEATURE:
<223> OTHER INFORMATION: Synthetic Construct

<400> SEQUENCE: 20
gctcaagtgc tgacccagac tccagcctcc gtgtctgcag ctgtgggagg cacagtcacc      60
atcaagtgcc aggccagtga ggatattagc aagtacttat cctggtatca gcagaaacca     120
gggcagcgcc ccaaactcct gatctattat gtatccaatc tggaatttgg ggtcccatcg     180
cggttcaaag gcagtggatc tgggacagag tacactctca ccatcagcga cctggagtgt     240
gacgatgctg ccacttacta ctgtcaccag ggttataccg gtgttaatgt tgaaaatgtt     300
ttcggcggag ggaccgaggt ggtggtcaga ggtgatccag ttgcacctac tgtcctcatc     360
ttcccaccag ctgctgatca agtcgcaaca ggtactgtga cgatcgtgtg tgtcgcgaac     420
aaatactttc ccgacgtgac cgtgacgtgg gaagtcgacg aacaacccca gacgaccggg     480
atcgaaaact caaagacccc gcaaaactcg gccgattgca catacaattt gtcctctacg     540
cttacactca cgtcgacgca gtacaatagt cacaaggagt atacatgcaa agttactcaa     600
ggaactacga gcgtggtcca gtcattcaat agaggggatt gt                        642
```

```
<210> SEQ ID NO 21
<211> LENGTH: 112
<212> TYPE: PRT
<213> ORGANISM: Artificial Sequence
<220> FEATURE:
<223> OTHER INFORMATION: Synthetic Construct

<400> SEQUENCE: 21

Gln Ser Val Glu Glu Ser Gly Gly Gly Leu Val Thr Pro Gly Gly Ser
1               5                   10                  15

Leu Thr Leu Thr Cys Thr Val Ser Gly Ile Asp Leu Thr Thr Tyr Ala
            20                  25                  30

Met Gly Trp Val Arg Gln Ala Pro Gly Glu Gly Leu Glu Trp Ile Gly
            35                  40                  45

Ile Ile Gly Gly Gly Gly Arg Thr Tyr Tyr Ala Ala Trp Ala Lys Gly
    50                  55                  60

Arg Phe Thr Ile Ser Lys Thr Ser Thr Thr Val Asp Leu Arg Ile Thr
65                  70                  75                  80

Ser Pro Ala Thr Glu Asp Thr Ala Thr Tyr Phe Cys Val Arg Gly Gly
                85                  90                  95
```

```
Asp Phe Phe Asp Leu Trp Gly Pro Gly Thr Leu Val Thr Val Ser Ser
            100                 105                 110
```

```
<210> SEQ ID NO 22
<211> LENGTH: 13
<212> TYPE: PRT
<213> ORGANISM: Artificial Sequence
<220> FEATURE:
<223> OTHER INFORMATION: Synthetic Construct

<400> SEQUENCE: 22

Thr Val Ser Gly Ile Asp Leu Thr Thr Tyr Ala Met Gly
1               5                   10
```

```
<210> SEQ ID NO 23
<211> LENGTH: 9
<212> TYPE: PRT
<213> ORGANISM: Artificial Sequence
<220> FEATURE:
<223> OTHER INFORMATION: Synthetic Construct

<400> SEQUENCE: 23

Ile Ile Gly Gly Gly Gly Arg Thr Tyr
1               5
```

```
<210> SEQ ID NO 24
<211> LENGTH: 9
<212> TYPE: PRT
<213> ORGANISM: Artificial Sequence
<220> FEATURE:
<223> OTHER INFORMATION: Synthetic Construct

<400> SEQUENCE: 24

Val Arg Gly Gly Asp Phe Phe Asp Leu
1               5
```

```
<210> SEQ ID NO 25
<211> LENGTH: 110
<212> TYPE: PRT
<213> ORGANISM: Artificial Sequence
<220> FEATURE:
<223> OTHER INFORMATION: Synthetic Construct

<400> SEQUENCE: 25

Ala Gln Val Leu Thr Gln Thr Pro Ala Ser Val Ser Ala Ala Val Gly
1               5                   10                  15

Gly Thr Val Thr Ile Lys Cys Gln Ala Ser Glu Asp Ile Ser Lys Tyr
                20                  25                  30

Leu Ser Trp Tyr Gln Gln Lys Pro Gly Gln Arg Pro Lys Leu Leu Ile
            35                  40                  45

Tyr Tyr Val Ser Asn Leu Glu Phe Gly Val Pro Ser Arg Phe Lys Gly
        50                  55                  60

Ser Gly Ser Gly Thr Glu Tyr Thr Leu Thr Ile Ser Asp Leu Glu Cys
65                  70                  75                  80

Asp Asp Ala Ala Thr Tyr Tyr Cys His Gln Gly Tyr Thr Gly Val Asn
                85                  90                  95

Val Glu Asn Val Phe Gly Gly Gly Thr Glu Val Val Val Arg
            100                 105                 110
```

```
<210> SEQ ID NO 26
<211> LENGTH: 11
<212> TYPE: PRT
<213> ORGANISM: Artificial Sequence
<220> FEATURE:
```

-continued

```
<223> OTHER INFORMATION: Synthetic Construct

<400> SEQUENCE: 26

Gln Ala Ser Glu Asp Ile Ser Lys Tyr Leu Ser
1               5               10

<210> SEQ ID NO 27
<211> LENGTH: 8
<212> TYPE: PRT
<213> ORGANISM: Artificial Sequence
<220> FEATURE:
<223> OTHER INFORMATION: Synthetic Construct

<400> SEQUENCE: 27

Tyr Tyr Val Ser Asn Leu Glu Phe
1               5

<210> SEQ ID NO 28
<211> LENGTH: 12
<212> TYPE: PRT
<213> ORGANISM: Artificial Sequence
<220> FEATURE:
<223> OTHER INFORMATION: Synthetic Construct

<400> SEQUENCE: 28

His Gln Gly Tyr Thr Gly Val Asn Val Glu Asn Val
1               5               10

<210> SEQ ID NO 29
<211> LENGTH: 20
<212> TYPE: PRT
<213> ORGANISM: Artificial Sequence
<220> FEATURE:
<223> OTHER INFORMATION: Synthetic Construct

<400> SEQUENCE: 29

Met Glu Thr Asp Thr Leu Leu Leu Trp Val Leu Leu Leu Trp Val Pro
1               5               10              15

Gly Ser Thr Gly
            20
```

ANTIBODIES THAT BIND HUMAN AND MOUSE INSL5 AND ENCODING NUCLEIC ACIDS THEREOF

CROSS RELATED APPLICATIONS

This application is the US national stage of International Patent Application No. PCT/US2021/044304 filed on Aug. 3, 2021 which claims the benefit of U.S. Provisional Application No. 63/060,701 filed on Aug. 4, 2020.

SEQUENCE LISTING

The application contains a Sequence Listing which has been submitted electronically in txt file format in its entirety named X22808SequenceListing.txt and is 25000 bytes in size and is hereby incorporated by reference.

The present invention relates to the field of medicine. More particularly, the present invention relates to compounds, diagnostics, and methods which include an antibody or fragment thereof directed against human or mouse insulin-like peptide-5 (INSL5). The compounds and methods of the present invention are expected to be useful in the field of oncology, reproductive, and metabolic diseases, e.g., diabetes and obesity, including diagnostics relating thereto.

The gut hormone INSL5 belongs to the Relaxin/Insulin-like family of peptides. Like the other INSL family members, INSL5 is composed of B- and A-chains connected by two disulfide bonds. INSL5 is expressed in various tissues; however, it is primarily co-secreted with other hormones from specialized enteroendocrine cells (EECs), called L cells, in the distal intestine, particularly in the colon and rectum. These cells regulate metabolic and physiological processes such as intestinal motility, hormone secretion, glucose homeostasis and appetite. INSL5 is the ligand for the receptor RXFR4/GPCR142/GPR100 and its receptor-ligand interaction results in the inhibition of intracellular cAMP levels. While INSL5 is considered an orexigenic (appetite-stimulating) hormone and its secretion is elevated by calorie restriction, the biological consequences of the INSL5-RXFP4 activated signaling pathway remain largely elusive.

In order to study INSL5, reliable and sensitive assays for INSL5 are needed. INSL5 has been studied in patients with metabolic dysfunction, polycystic ovarian syndrome (PCOS), colorectal cancer (CRC), and infertility, and pre-clinical models of these diseases. However, there remains a need to provide antibodies that bind human and mouse INSL5 to study these effects further. In particular, there remains a need for INSL5 antibodies with high affinities to both human and mouse INSL5. Currently available assays have sensitivity, reproducibility, performance, and/or quantitative issues. Thus, additional methods of testing human or mouse samples are needed.

In a specific embodiment of the present disclosure, antibodies are provided which bind INSL5 comprising a heavy chain variable region (VH) and a light chain variable region (VL), wherein the VH comprises heavy chain complementarity determining regions (HCDR) HCDR1, HCDR2, and HCDR3, and the VL comprises light chain complementarity determining regions (LCDR) LCDR1, LCDR2, and LCDR3, wherein the HCDR1 comprises TASGGFSLSSYDMG (SEQ ID NO:10), the HCDR2 comprises TISAGGYTY (SEQ ID NO:11), the HCDR3 comprises ARERWNY-DRSGGAGSGYFDL (SEQ ID NO:12), the LCDR1 comprises QASQSITSSYLS (SEQ ID NO:14), the LCDR2 comprises YPAANLAS (SEQ ID NO:15), and the LCDR3 comprises LYGYFSSSIDFA (SEQ ID NO:16). According to some embodiments, antibodies of the present disclosure comprise a VH that comprises SEQ ID NO:9 and a VL which comprises SEQ ID NO:13. According to some embodiments, the antibodies of the present disclosure comprise a heavy chain (HC) comprising SEQ ID NO:5 and a light chain (LC) comprising SEQ ID NO:7. According to some embodiments, antibodies of the present disclosure comprise a heavy chain (HC) comprising amino acids 2-446 of SEQ ID NO:5, and a light chain (LC) comprising SEQ ID NO:7. According to some embodiments, the antibodies of the present disclosure comprise a HC consisting of SEQ ID NO:5 and a LC consisting of SEQ ID NO:7.

According to some embodiments, the present disclosure provides a nucleic acid comprising a sequence encoding SEQ ID NO:5 or SEQ ID NO:7, or both. According to some embodiments, one or more vectors comprise one or more nucleic acids encoding SEQ ID NO:5 or SEQ ID NO:7, or both. According to some embodiments, the present disclosure provides a composition comprising a first vector comprising a nucleic acid sequence encoding SEQ ID NO:5 and a second vector comprising a nucleic acid sequence encoding SEQ ID NO:7. According to other embodiments, the present disclosure provides a composition comprising a vector comprising a nucleic acid encoding SEQ ID NO:5 and SEQ ID NO:7. In another embodiment, the present disclosure provides a cell comprising one or more vectors comprising one or more nucleic acids encoding SEQ ID NO:5 or SEQ ID NO:7, or both. According to some embodiments, the present disclosure provides a cell comprising a first vector comprising a nucleic acid sequence encoding SEQ ID NO:5 and a second vector comprising a nucleic acid sequence encoding SEQ ID NO:7. According to other embodiments, the present disclosure provides a cell comprising a vector comprising a nucleic acid encoding SEQ ID NO:5 and a second nucleic acid sequence encoding SEQ ID NO:7. In further embodiments, the cell is a mammalian cell.

In a specific embodiment of the present disclosure, antibodies are provided which bind INSL5 comprising a heavy chain variable region (VH) and a light chain variable region (VL), wherein the VH comprises heavy chain complementarity determining regions (HCDR) HCDR1, HCDR2, and HCDR3, and the VL comprises light chain complementarity determining regions (LCDR) LCDR1, LCDR2, and LCDR3, wherein the HCDR1 comprises TVSGIDLTTYAMG (SEQ ID NO:22), the HCDR2 comprises IIGGGGRTY (SEQ ID NO:23), the HCDR3 comprises VRGGDFFDL (SEQ ID NO:24), the LCDR1 comprises QASEDISKYLS (SEQ ID NO:26), the LCDR2 comprises YYVSNLEF (SEQ ID NO:27), and the LCDR3 comprises HQGYTGVNVENV (SEQ ID NO:28).

According to some embodiments, antibodies of the present disclosure comprise a VH that comprises SEQ ID NO:21 and a VL that comprises SEQ ID NO:25. In a further embodiment, the antibodies of the present disclosure comprise a heavy chain (HC) comprising SEQ ID NO:17 and a light chain (LC) comprising SEQ ID NO:19. In some embodiments, antibodies of the present disclosure comprise a heavy chain (HC) comprising amino acids 2-435 of SEQ ID NO:17, and a light chain (LC) comprising SEQ ID NO:19. According to some embodiments, antibodies of the present disclosure comprise a HC consisting of SEQ ID NO:17 and a LC consisting of SEQ ID NO:19.

According to some embodiments, the present disclosure provides a nucleic acid comprising a sequence encoding SEQ ID NO:17 or SEQ ID NO:19, or both. According to some embodiments, one or more vectors comprise one or more nucleic acids encoding SEQ ID NO:17 or SEQ ID NO:19, or both. According to some embodiments, the present disclosure provides a composition comprising a first vector comprising a nucleic acid sequence encoding SEQ ID NO:17 and a second vector comprising a nucleic acid sequence encoding SEQ ID NO:19. According to some embodiments, the present disclosure provides a composition comprising a vector comprising a nucleic acid encoding SEQ ID NO:17 and SEQ ID NO:19. In another embodiment, the present disclosure provides a cell comprising one or more vectors comprising one or more nucleic acids encoding SEQ ID NO:17 or SEQ ID NO:19, or both. According to some embodiments, the present disclosure provides a cell comprising a first vector comprising a nucleic acid sequence encoding SEQ ID NO:17 and a second vector comprising a nucleic acid sequence encoding SEQ ID NO:19. According to other embodiments, the present disclosure provides a cell comprising a vector comprising a nucleic acid encoding SEQ ID NO:17 and a second nucleic acid sequence encoding SEQ ID NO:19. In further embodiments, the cell is a mammalian cell.

According to some embodiments, antibodies of the present disclosure bind to human INSL5. According to some embodiments, antibodies of the present disclosure bind to the A chain (SEQ ID NO:1) and the B chain (SEQ ID NO:2) of human INSL5. According to some embodiments, antibodies of the present disclosure bind to mouse INSL5. According to some embodiments, antibodies of the present disclosure bind to the A chain (SEQ ID NO:3) and the B chain (SEQ ID NO:4) of mouse INSL5.

According to some embodiments, the present invention provides a process of producing an antibody comprising culturing the cell under conditions such that the antibody is expressed and recovering the expressed antibody from the culture medium. According to some embodiments, the present invention provides a process of producing an antibody produced by culturing the cell under conditions such that the antibody is expressed and recovering the expressed antibody from the culture medium.

According to further embodiments of the present disclosure, a method of detecting human or mouse INSL5 in a sample is provided. Such methods comprise the steps of contacting the sample with an antibody of the present disclosure that specifically binds human or mouse INSL5 and detecting a signal by said step of contacting.

According to some embodiments, a method of quantifying human or mouse INSL5 in a sample is provided. Such methods comprise the steps of contacting said sample with an antibody of the present disclosure that specifically binds INSL5 and detecting a signal by said step of contacting. In some embodiments, such methods further comprise the steps of contacting a control standard with the antibody and detecting a signal provided by said step of contacting the control standard.

According to some embodiments of the methods of the present disclosure, such methods further comprise the step of quantifying INSL5 in the sample. In such embodiments, the step of quantifying INSL5 comprises quantifying INSL5 in the sample when compared to a reference standard.

According to some embodiments of the present disclosure, the sample is one of blood, plasma, serum, or cerebrospinal fluid (CSF).

According to some embodiments of the methods of the present disclosure, the methods further comprise the step of contacting the sample with an antibody that specifically binds human or mouse INSL5 and a second antibody, said second antibody also binds human or mouse INSL5. In some such methods, one of the antibody or the second antibody comprises a detectable label and said step of detecting comprises detecting a signal provided by the detectable label upon formation of a complex comprising the antibody, the second antibody, and human or mouse INSL5. According to some such embodiments, one of the antibody and the second antibody are immobilized on a substrate. In some embodiments of the methods of the present disclosure, the steps of contacting the sample with the antibody and contacting the sample with the second antibody happen simultaneously. According to some more specific embodiments, the second antibody comprises an antibody of the present disclosure that specifically binds human or mouse INSL5 as disclosed herein.

According to some embodiments of the methods of the present disclosure, the methods further comprise the step of contacting the sample with an antibody that specifically binds INSL5 and a second antibody, and said second antibody specifically also binds INSL5. In some such methods, one of the antibody or the second antibody comprises a detectable label and said step of detecting comprises detecting a signal provided by the detectable label upon formation of a complex comprising the antibody, the second antibody and INSL5. According to some such embodiments, one of the antibody and the second antibody are immobilized on a substrate. In other embodiments, the second antibody binds a different epitope of INSL5. In some embodiments of the methods of the present disclosure, the steps of contacting the sample with the antibody and contacting the patient sample with the second antibody occurs simultaneously. In any such embodiments, the antibody or the second antibody, or both, is an antibody that binds INSL5 as disclosed herein.

The term "antibody," as used herein, refers to an immunoglobulin molecule that binds an antigen. Embodiments of an antibody include a monoclonal antibody, polyclonal antibody, human antibody, humanized antibody, or chimeric antibody. The antibodies can be of any class (e.g., IgG, IgE, IgM, IgD, IgA), and any subclass (e.g., IgG1, IgG2, IgG3, IgG4).

An exemplary antibody of the present disclosure is an immunoglobulin G (IgG) type antibody comprised of four polypeptide chains: two heavy chains (HC) and two light chains (LC) that are cross-linked via inter-chain disulfide bonds. The amino-terminal portion of each of the four polypeptide chains includes a variable region of about 100-125 or more amino acids primarily responsible for antigen recognition. The carboxyl-terminal portion of each of the four polypeptide chains contains a constant region primarily responsible for effector function. Each heavy chain is comprised of a heavy chain variable region (BH) and a heavy chain constant region. Each light chain is comprised of a light chain variable region (VL) and a light chain constant region. The IgG isotype may be further divided into subclasses (e.g., IgG1, IgG2, IgG3, and IgG4).

The VH and VL regions can be further subdivided into regions of hyper-variability, termed complementarity determining regions (CDRs), interspersed with regions that are more conserved, termed framework regions (FR). The CDRs are exposed on the surface of the protein and are important regions of the antibody for antigen binding specificity. Each VH and VL is composed of three CDRs and four FRs, arranged from amino-terminus to carboxyl-terminus in the following order: FR1, CDR1, FR2, CDR2, FR3, CDR3, FR4. Herein, the three CDRs of the heavy chain are referred to as "HCDR1, HCDR2, and HCDR3" and the three CDRs of the light chain are referred to as "LCDR1, LCDR2 and LCDR3." The CDRs contain most of the residues that form specific interactions with the antigen. Assignment of amino acid residues to the CDRs may be done according to the well-known schemes, including those described in Kabat (Kabat et. al, "Sequences of Proteins of Immunological Interest," National Institutes of Health, Bethesda, Md. (1991)), Chothia (Chothia et. al., "Canonical structures for the hypervariable regions of immunoglobulins", Journal of Molecular Biology, 196, 901-917 (1987); Al-Lazikani et. al., "Standard Conformations for the canonical structures of immunoglobulins", Journal of Molecular Biology, 273, 927-948 (1997)), North (North et. al, "A New Clustering of Antibody CDR Loop Conformations", Journal of Molecular Biology, 406, 228-256 (2011)), or IMGT (the international ImMunoGeneTics database available at www.imgt.org; see Lefranc et. al., Nucleic Acids Res. 1999; 27:209-212). Assignment of amino acids to CDR domains within the LCVR and HCVR regions of the antibodies of the present invention is based on North. LCs, according to some embodiments of the present disclosure, are classified as kappa or lambda and are each characterized by a particular constant region as known in the art. HCs, according to some embodiments of the present disclosure, are classified as gamma, mu, alpha, delta, or epsilon, and define the isotype of an antibody as IgG, IgM, IgA, IgD, or IgE, respectively. According to some embodiments, the antibodies include IgG HCs, which can be further divided into subclasses, e.g., IgG1, IgG2, IgG3, IgG4. The carboxy-terminal portion of each HC defines a constant region primarily responsible for effector function. In a particular embodiment, the antibodies of the present invention have one or more modifications in the constant region of each HC that reduces effector function.

The antibodies of the present invention are monoclonal antibodies. Monoclonal antibodies are antibodies derived from a single copy or clone including, for example, any eukaryotic, prokaryotic or phage clone, and not the method by which it is produced. Monoclonal antibodies can be produced, for example, by hybridoma technologies, recombinant technologies, phage display technologies, synthetic technologies, e.g., CDR-grafting, or combinations of such or other technologies known in the art.

Methods of producing and purifying antibodies are well known in the art and can be found, for example, in Harlow and Lane (1988), *Antibodies, A Laboratory Manual*, Cold Spring Harbor Laboratory Press, Cold Spring harbor, N.Y., chapters 5-8 and 15, ISBN 0-87969-314-2. For example, mice or rabbits may be immunized with human or mouse INSL5 and the resulting antibodies can be recovered, purified, and the amino acid sequences determined using conventional methods well known in the art. Likewise, a phage library may be screened, whereby thousands of Fab fragments are screened for interaction with human or mouse INSL5 and resulting interactions can be recovered, purified, and the amino acid sequences determined using conventional methods well known in the art, whereby initial lead antibodies can be constructed.

In particular embodiments of the present invention, the antibody, or the nucleic acid encoding same, is provided in isolated form. As used herein, the term "isolated" refers to a protein, peptide, or nucleic acid that is free or substantially free from other macromolecular species found in a cellular environment.

The term "bind" and "binds" as used herein are intended to mean, unless indicated otherwise, the ability of a protein or molecule to form a chemical bond or attractive interaction with another protein or molecule, which results in proximity of the two proteins or molecules as determined by common methods known in the art.

Anti-INSL5 antibodies of the present disclosure that bind to human or mouse INSL5 can be used to isolate and/or detect isoforms of human or murine INSL5 by techniques such as affinity chromatography, immunoprecipitation, immunohistochemistry or ELISA-based assay. Such assay can be used to detect and/or evaluate the abundance and/or patterns of INSL5 for diagnostic, prognostic, or theranostic purposes to monitor polypeptide levels, for example in serum, plasma, blood or CSF as part of a clinical testing procedure, e.g., to determine the efficacy of a given treatment regimen. As understood in the art, an antibody of the present invention may be coupled to a detectable substance or label to facilitate its detection. Examples of detectable substances or labels include various enzymes, prosthetic groups, fluorescent materials, luminescent materials, bioluminescent materials, chemiluminescent materials and radioactive materials. Examples of suitable enzymes include horseradish peroxidase, alkaline phosphatase, beta-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotnazinylamine fluorescein, dansyl chloride or phycoerythrin; an example of a luminescent material includes luminol; examples of bioluminescent materials include luciferase, luciferin, ruthenium and aequorin, and examples of suitable radioactive material include $^{125}$I, $^{131}$I, $^{35}$S or $^{3}$H. Antibodies of the present invention can also be useful in pharmacogenomic analysis. Such embodiments may be used to identify individuals that can benefit from specific or modified treatment modalities and/or monitor efficacy of present treatment regimens.

A "control standard," as used herein, refers to a sample that can be used to compare the results obtained from a sample in the methods of the invention. Control standards can be cells, blood, plasma, CSF, tissue or known protein concentrations spiked into a media. The concentration levels in a control standard can be an absolute or relative amount, a range of amount, or a minimum amount, a mean amount, and/or a median amount of INSL5. A control standard can also serve as a baseline of INSL5 to which the patient sample is compared. The control standard can include a concentration value from the same patient or a known, normal reference of INSL5. Further, in some embodiments, a control standard may express INSL5 concentrations in the form of a standard curve.

As used herein, the term capture antibody refers to an antibody that will bind INSL5. In such embodiments, the capture antibody is capable of binding and capturing INSL5, for example specifically binding INSL5 in a sample under suitable conditions, such that the capture antibody-INSL5 complex can be separated from the rest of the sample. In some embodiments, the capture antibody may be an antibody that specifically binds to INSL5 and an antibody that specifically binds INSL5 is used as the second (or detection) antibody. In further embodiments, the capture antibody is an antibody provided herein. In further embodiments, the capture antibody is an antibody with HCDRs corresponding to SEQ ID NOs:10-12 and LCDRs corresponding to SEQ ID NOs:14-16, respectively. In further embodiments, the capture antibody is an antibody with HCDRs corresponding to SEQ ID NOs:22-24 and LCDRs corresponding to SEQ ID NOs:26-28, respectively. In some embodiments, the capture antibody is immobilized. In some embodiments, the detection antibody is labeled with a detectable label. In some embodiments, the second (or detection) antibody is an antibody provided herein. In further embodiments, the second (or detection) antibody is an antibody with HCDRs corresponding to SEQ ID NOs:10-12 and LCDRs corresponding to SEQ ID NOs:14-16, respectively. In further embodiments, the second (or detection) antibody is an antibody with HCDRs corresponding to SEQ ID NOs:22-24 and LCDRs corresponding to SEQ ID NOs:26-28, respectively.

In some embodiments, the capture antibody is immobilized in a "sandwich" immunoassay, and the capture or first antibody specifically binds to human or mouse INSL5. In some such embodiments, the capture antibody is an antibody of the present invention that specifically binds human or mouse INSL5. In further embodiments, the capture antibody is an antibody with HCDRs corresponding to SEQ ID NOs:10-12 and LCDRs corresponding to SEQ ID Nos:14-16. In further embodiments, the capture antibody is an antibody with HCDRs corresponding to SEQ ID NOs:22-24 and LCDRs corresponding to SEQ ID NOs:26-28. In such sandwich immunoassays, a detection (or second) antibody is also utilized. According to some embodiments, a detection or second antibody may bind specifically to the capture antibody and may be labelled with a detectable label. In some embodiments, the detection of second antibody specifically binds to human or mouse INSL5 already bound, or captured, by the capture or first antibody. In some such embodiments, the second antibody is an antibody of the present invention that specifically binds human or mouse INSL5. In some embodiments, the second (or detection) antibody is an antibody provided herein. In further embodiments, the second (or detection) antibody is an antibody with HCDRs corresponding to SEQ ID NOs:10-12 and LCDRs corresponding to SEQ ID NOs:14-16. In further embodiments, the second (or detection) antibody is an antibody with HCDRs corresponding to SEQ ID NOs:22-24 and LCDRs corresponding to SEQ ID NOs:26-28.

As used herein, a "detectable label" is a moiety, composition or technique that can be used to detect the formation of a complex between an antibody of the present invention that specifically binds to the A and B chains of human or mouse INSL5. According to some embodiments, the detectable label may be conjugated to the antibody (either capture or detection, as the case may be) directly or indirectly. Exemplary embodiments of detectable labels include biotin; radioisotopes; fluorophores or other fluorescent moieties; and enzymatic moieties.

Antigen-binding fragments of such antibodies include, for example, Fab fragments, Fab' fragments, F(ab')₂ fragments, and single chain Fv fragments.

"Framework region" or "framework sequence" refers to any one of framework regions 1 to 4. Humanized antibodies and antigen-binding fragments thereof encompassed by the present invention include molecules wherein any one or more of framework regions 1 to 4 is humanized, i.e., wherein any of the possible combinations of individual humanized regions 1 to 4, is present. For example, this includes molecules in which framework region 1 and framework region 2, framework region 1 and framework region 3, framework region 1, 2, and 3, etc., are humanized. Humanized frameworks are those that have at least about 80% sequence identity to a known human germline framework sequence. Human framework germline sequences can be obtained from ImMunoGeneTics (IMGT) or from *The Immunoglobulin FactsBook* by Marie-Paule Lefranc and Gerard Lefranc, Academic Press, 2001, ISBN 012441351. For example, germline light chain frameworks can be selected from the group consisting of A11, A17, A18, A19, A20, A27, A30, L1, L11, L12, L2, L5, L15, L6, L8, O12, O2, and O8, and germline heavy chain framework regions can be selected from the group consisting of VH2-5, VH2-26, VH2-70, VH3-20, 25 VH3-72, VH1-46, VH3-9, VH3-66, VH3-74, VH4-31, VHI-18, VHI-69, VI-13-7, VH3-11, VH3-15, VH3-21, VH3-23, VH3-30, VH3-48, VH4-39, VH4-59, and VH5-51.

Protein "INSL5" (also known as insulin-like peptide-5) refers to a gut hormone encoded by the Insl5 gene. INSL5 is a peptide produced in enteroendocrine cells of the distal colon in humans and mice.

The results of the following assays demonstrate that the exemplified monoclonal antibodies and antigen-binding fragments thereof of the present invention bind and/or neutralize INSL5 and therefore may be used for diagnostic assays, including, but not limited to sandwich ELISA assays in order to study the role of INSL5 in metabolic diseases including, but not limited to, diabetes and obesity.

Disclosed herein are antibodies for use in diagnostics, such as diagnostic assays to detect the presence or level of INSL5.

EXAMPLES

The following non-limiting examples are offered for purposes of illustration, not limitation.

Example 1: Recombinant Expression of Antibody I

Antibody I is an antibody having a heavy chain amino acid sequence of SEQ ID NO:5 and a light chain amino acid sequence of SEQ ID NO:7.

Antibody I is generated in a mammalian cell expression system using CHO-K1 cell derivatives (Lonza Biologics Inc.). cDNA sequences encoding SEQ ID NO:5 and SEQ ID NO:7 are sub-cloned into GS-containing expression plasmid backbones (pEE12.4-based plasmids; Lonza Biologics Inc.). Each cDNA sequence is fused in frame with the coding sequence of a signal peptide sequence, METDTLLL-WVLLLWVPGSTG (SEQ ID NO:29), to enhance secretion of the antibody into the tissue culture medium. The expression of both cDNA sequences is driven by the viral CMV promoter.

For generating the antibody via transient transfection, CHO-K1 cells are transfected with an equal stoichiometric ratio of the recombinant expression plasmids using a PEI-based method. Briefly, the appropriate volume of CHO-K1 suspension cells at a density of 4×10⁶ cells/mL is transferred in shake flasks, and both PEI and recombinant plasmid DNA are added to the cells. Cells are incubated in a suspension culture at 32° C. for 6 days. At the end of the incubation period, cells are removed by low speed centrifugation and the antibody is purified from the conditioned medium.

The antibody secreted into the media from the CHO-K1 cells, is purified by Protein A affinity chromatography followed by size-exclusion chromatography (SEC) and/or ion exchange chromatography. Specifically, the antibody from harvested media is captured onto Mab Select Protein A resin (GE). The resin then is briefly washed with a running buffer, such as a phosphate-buffered saline (PBS; pH 7.4) to remove non-specifically bound material. The protein is eluted from the resin with a low pH solution, such as 10 mM citric acid pH 3. Fractions containing the antibody are pooled and may be held at a low pH to inactivate potential viruses. They may be neutralized by adding a base such as 0.1 M Tris pH 8.0.

The antibody is further purified by SEC by loading the concentrated Protein A pool on a Superdex200 (GE Healthcare) with isocratic elution in PBS pH 7.4. The antibody may be further purified by an ion exchange chromatography step using resins such as Poros 50 HS (ThermoFisher). In that case the antibody is eluted from the column using a 0 to 500 mM NaCl gradient in 20 mM NaOAc, pH 5.0 over 15 column volumes. The purified antibody may be buffer exchanged to PBS pH 7.4 and concentrated for example by using centrifugal filter units (such as Amicon Ultra 50K centrifugal filter units) or by tangential flow ultrafiltration on a regenerated cellulose membranes (Millipore).

The antibody therefore is prepared in this manner or in a similar manner that would be readily determined by one of skill in the art.

Example 2: Recombinant Expression of Antibody II

Antibody II is an antibody having a heavy chain amino acid sequence of: (SEQ ID NO:17) and a light chain amino acid sequence of: (SEQ ID NO:19).

Here, the antibody of SEQ ID NO:17 and SEQ ID NO:19 is generated essentially as described for Example 1 except that cDNA sequences encoding SEQ ID NOs:17 and 19 are used in the expression plasmids.

In Vitro Function

Example 3: Antibody Binding to Human and Mouse INSL5 Via SPR

In vitro binding of the antibodies of Examples 1 and 2 to human and mouse INSL5 is determined by Surface Plasmon Resonance (SPR) at 25° C. and at 37° C. In particular, the affinity of the antibodies of Examples 1 and 2 is summarized below in Tables 1 and 2.

Binding of the antibodies of Examples 1 and 2 to human and mouse INSL5 is carried out on a Biacore 8K (GE Healthcare) instrument. 1×HBS-EP+ (10 mM HEPES pH 7.6, 150 mM NaCl, 3 mM EDTA, 0.05% Polysorbate 20) (Teknova) is used as a running buffer. Protein A (Calbiochem #539202-5 mg) immobilization onto a Series S Sensor Chip CM5 (GE Healthcare) is performed according to the manufacturer's instructions (Amine Coupling Kit BR-1000-50) at 25° C. Briefly, carboxyl groups on the sensor chip surfaces (flow cell 1 and 2) are activated by injecting 70 μL of a mixture containing 75 mg/mL EDC and 11.5 mg/mL NHS at 10 μL/min. A solution of 50 μg/mL of Protein A is prepared by diluting 10 μl of a 5 mg/mL stock solution into 1 mL 10 mM sodium acetate pH 4.5. 70 μL of this solution is injected over the activated chip surfaces (flow cell 1 and 2, channels 1 to 8) at 10 μL/min for 7 min. Excess reactive groups on the surfaces (flow cell 1 and 2) are then deactivated by injecting 70 μL of 1 M ETA HCl—NaOH pH 8.5 at 10 μL/min. The chip is conditioned by six 15 s injections of 10 mM glycine-HCl pH 1.5 at 30 μL/min.

Human INSL5 (Phoenix Pharmaceuticals Cat #035-70A) and mouse INSL5 (Phoenix Pharmaceuticals 035-40) are reconstituted at 0.5 (99 μM) or 1 mg/mL (195 μM) in DMSO, respectively. A 2-fold dilution series of the peptides is being made in 1×HBS-EP+ buffer at concentrations of 20, 10, 5, 2.5, 1.25, 0.625, 0.313, 0.156, and 0 nM. The antibodies of Example 1, 2, or a negative control are prepared by diluting them to 1 μg/mL in 1×HBS-EP+ buffer.

The experiment is conducted at 25° C. as well as at 37° C. and initiated with 5 start-up cycles of injecting 1×HBS-EP+ buffer. Then in each cycle, the antibody is captured onto flow cell 2 of channels 1-8 at 10 μL/min for 20 seconds. Next, 180 μL of the respective INSL5 peptide sample is individually injected across flow cells 1 and 2 for 180 seconds at 60 μL/min and then let dissociate for 1200 seconds at 60 μL/min flow rate. The surface is regenerated by injecting two 15 second pulses of 10 mM glycine-HCl pH 1.5 (BR-1003-54) at 30 μL/min. After a stabilization period of 60 seconds at a flow rate of 60 μL/min the next cycle is started.

The resulting sensorgrams are analyzed using Biacore 8K Evaluation Software). 1:1 binding kinetics model fitting is used to calculate the binding kinetic parameters association rate (ka), dissociation rate (kd), and equilibrium dissociation constant ($K_D$).

TABLE 1

| Binding Kinetics of Antibody I and Antibody II to Human and Mouse INSL5 at 25° C. | | | | | | |
|---|---|---|---|---|---|---|
| | Human INSL5 | | | Mouse INSL5 | | |
| 25° C. | ka (1/Ms) | kd (1/s) | $K_D$ (M) | ka (1/Ms) | kd (1/s) | $K_D$ (M) |
| Antibody I | 8.8E+06 | 3.6E−04 | 4.1E−11 | 1.2E+07 | 5.4E−05 | 4.6E−12 |
| Antibody II | 1.6E+07 | 3.4E−04 | 2.1E−11 | 1.8E+07 | 1.1E−04 | 6.1E−12 |

For Antibody I, $K_D$ at 25° C. is determined as 41 pM to human INSL5 and 4.6 pM to mouse INSL5. For Antibody II, $K_D$ at 25° C. is determined as 21 pM to human INSL5 and 6.1 pM to mouse INSL5.

TABLE 2

| Binding Kinetics of Antibody I and Antibody II to Human and Mouse INSL5 at 37° C. | | | | | | |
|---|---|---|---|---|---|---|
| | Human INSL5 | | | Mouse INSL5 | | |
| 37° C. | ka (1/Ms) | kd (1/s) | $K_D$ (M) | ka (1/Ms) | kd (1/s) | $K_D$ (M) |
| Antibody I | 2.4E+07 | 2.6E−03 | 1.1E−10 | 2.3E+07 | 1.5E−04 | 6.7E−12 |
| Antibody II | 4.0E+07 | 3.3E−03 | 8.1E−11 | 5.1E+07 | 7.2E−04 | 1.4E−11 |

For Antibody I, $K_D$ at 37° C. is determined as 110 pM to human INSL5 and 6.7 pM to mouse INSL5. For Antibody II, $K_D$ at 37° C. is determined as 81 pM to human INSL5 and 14 pM to mouse INSL5.

Example 4: In Vitro Neutralization of INSL5 Activity Increases cAMP Production In vitro neutralization of human and mouse INSL5 activity with Antibody I and Antibody II is determined with a cAMP dynamic 2 Assay (Cisbio Cat #62AM4PEJ). The kit is based on HTRF technology that measures the cAMP accumulation in cells. Cells stimulated with a fixed concentration of forskolin increase cAMP production. Introducing a fixed concentration of human and/or mouse INSL5 to the cells inhibits the cAMP production by binding to the RXFP4 receptor. Antibody I and Antibody II bind and neutralize the effects of human and mouse INSL5 prior to binding to the RXFP4 receptor. $EC_{50}$ values derived from antibody serial dilution data of Antibody I and Antibody II are summarized below in Table 3 and demonstrate the increase of cAMP production as the concentration of antibodies increases. Preparation of cell plates: Mouse RXFP4 CHO-K1 cells (DiscoveRx Part #93-0929E2) and human CHO RXFP4 cells (DiscoveRx 93-0701E2) are thawed quickly in a 37° C. water bath and reconstituted with 500 μL of pre-warmed (in 37° C. water bath) Cell Plating Reagent 2 (DiscoveRx 93-0563R Series). Cells are mixed by pipetting up and down and then added to 11.5 mL of pre warmed (in 37° C. water bath) Cell Plating Reagent 2. Cells are plated at 8,000 cells/well at 100 μL per well in white full area plate (Corning-Costar 3917). The plates are incubated for 48 hours at 37° C. to allow cells to adhere to the plate. After 48 hours the growth media is aspirated and 40 μL of Cell Assay Buffer [HBSS (Hyclone SH30028.03), 20 mM HEPES (Hyclone SH30237.01), 1% FBS (Gibco 10438-026), 1 mM IBMX (Sigma 15879, diluted in DMSO)] are added to each well. 30 μL of the Compound Assay Buffer (HBSS+20 mM HEPES+1% FBS) containing 17 μM of Forskolin (Sigma Aldrich—CAS #F3917 (10 mM in DMSO)) are diluted into each well.

Preparation of samples (antibody-INSL5 peptide mixtures): Human INSL5 peptide (Phoenix Pharmaceuticals, Cat #035-70) or mouse INSL5 peptide (Phoenix Pharmaceuticals, Cat #035-40) are prepared at their respective $IC_{80}$ concentrations in Cell Plating Reagent 2. 10 μL of the respective INSL5 peptide (16 times the final concentration in the assay; i.e. 144 nM for mouse INSL5 and 1280 nM for human INSL5) are then mixed with 10 μL of a serial dilution of antibodies (starting at 160 nM) of Examples 1 or 2 (final antibody starting concentration is 10 nM). Samples are incubated at room temperature for two hours with moderate shaking in a PCR plate (Fisherbrand Cat #14230244).

Conducting the cell assay: 10 μL of the antibody-INSL5 peptide mixtures are added to the 70 μL of buffer mixture in the assay plates (containing the cells) and incubated at room temperature for 1 hour with moderate shaking. During the incubation, the cAMP detection reagents are prepared: 500 μL of cAMP-d2 and Anti-cAMP-Cryptate stock reagent solutions (cAMP dynamic 2 100,000 tests Kit Cat #62AM4PEJ) are diluted into 9.5 mL of Conjugate/Lysis Buffer each. After 1 hour incubation, 40 μL of the cAMP-d2 detection reagent is added to each well of the cell assay plate. Then immediately 40 μL of the Anti-cAMP-Cryptate detection reagent is added to the cell assay plate. The plate is incubated at room temperature for 1 hour with aluminum seal. Then the plate is read on Perkin Elmer Envision and the results are calculated from the machine's 665 nm/620 nm ratio.

Statistical analysis of data: Data is imported from the Perkin Elmer Envision reader into GRAPHPAD PRISM® software (GraphPad Software, LLC; La Jolla, CA). $EC_{50}$ values are generated by variable slope-four parameter dose response curve analysis. SEM is calculated by taking the $EC_{50}$ standard deviation between independent experiments (n) divided by the square root of independent experiments. GRAPHPAD PRISM® is a US registered trademark of GraphPad Software, LLC.

TABLE 3

| Neutralization of Human and Mouse INSL5 Activity Prior to Binding to the RXFP4 Receptor by Antibody I and Antibody II as Monitored by Increase in cAMP Production. | | | | | | |
| --- | --- | --- | --- | --- | --- | --- |
| | Human INSL5 | | | Mouse INSL5 | | |
| Neutralization | $EC_{50}$ (nM) | SEM | n | $EC_{50}$ (nM) | SEM | n |
| Antibody I | 4.35 | 0.49 | 2 | 0.84 | 0.12 | 3 |
| Antibody II | 1.27 | N/A | 1 | 0.45 | 0.01 | 2 |

For Antibody I, $EC_{50}$ is determined as 4.35 nM to human INSL5 and 0.84 nM to mouse INSL5. For Antibody II, $EC_{50}$ is determined as 1.27 nM to human INSL5 and 0.45 pM to mouse INSL5.

Example 5: Thermal Stability by TDF

Thermostability of Antibody I and Antibody II is determined by Thermal Denaturation Fluorimetry (TDF). Particularly, the melting temperature ($T_m$) for the Fc and Fab domains of antibodies of Examples 1 and 2 are reported in Table 4.

A thermofluor assay is run on a LIGHTCYCLER® 480II PCR machine using SYPRO® Orange dye (5000× concentrate, INVITROGEN® S6651). Excitation and emissions filters are set at 465 nm and 580 nm respectively and the temperature is ramped continuously from 25° C. to 95° C. at a rate of 1° C./s. Final assay conditions contain Examples 1 or 2 at 0.2 mg/mL and 10× SYPRO® Orange dye in PBS pH 7.4 (Corning 21-040-CV). SYPRO® is a US registered mark of Molecular Probes Inc. INVITROGEN® is a US registered trademark of Life Technologies Corporation. LIGHT-CYCLER® is a US registered trademark of Roche Diagnostics GMBH.

The experiment is performed by diluting Examples 1 or 2 to 0.4 mg/mL and mixing it in equal parts with 20× SYPRO® Orange dye in PBS pH 7.4 to reach a final volume of 30 μL per sample (BE05746-005). The mixture is dispensed as 6 μL aliquots in triplicate into a 384-multiwell assay plate (Roche 04-729-749-001). The $T_m$ values for Examples 1 and 2 are determined using the Thermal Shift Analysis Software (Roche) by the first derivative method. The analysis software smooths the raw fluorescence data and the $T_m$ is collected by determining the temperature where the upward slope of fluorescence vs. temperature is maximal (inflection point). Mean $T_m$ values and SD are calculated for each triplicate set.

TABLE 4

| Thermal Stability of Antibody I and Antibody II by TDF. | | | | |
| --- | --- | --- | --- | --- |
| | Fc Domain | | Fab Domain | |
| | Tm (° C.) | SD | Tm (° C.) | SD |
| Antibody I | 76.1 | 0.02 | 87.9 | 0.03 |
| Antibody II | 76.4 | 0.05 | 82.5 | 0.03 |

For Antibody I, the Tm is determined as 76.1° C. for the Fc domain and 87.9° C. for the Fab domain. For Antibody II, the Tm is determined as 76.4° C. for the Fc domain and 82.5° C. for the Fab domain.

Example 6: INSL5 Detection Assay

Antibody I and Antibody II are used to detect and quantify human and mouse INSL5 concentrations by sandwich ELISA. In particular, the detection range of this assay approximates between 30 pg/mL for the lower limit of detection and 100,000 pg/mL for the upper limit of detection as summarized below in Table 5.

Labeling of Antibody I with MSD® SulfoTag (NHS Ester 150 nmole, Cat #R91AN-1): MSD® Sulfo-Tag powder is resuspended in the original vial with 50 μL of ice cold Milli Q water, for a concentration of 3 nmol/μL. Using a labeling challenge ratio of 12, 2.7 μL of reagent are added to 100 μL of 1 mg/mL of antibody. The solution is mixed well and kept mixture out of light while shaking at room temperature for 2 hours. Towards the end of the incubation, a ZEBA® Spin Desalting column (Thermo Scientific Cat #87766) is prepared. The column is inverted until all resin is a homogenous mixture. The valve on bottom of column is opened and liquid is drained through centrifugation for 1 min at 1500×g. The column is washed three times with 500 µl of 1×PBS using 1 min 1500×g spins. After 2 hour incubation the antibody labeling reaction solution is added dropwise into the column resin. The column is placed into an Eppendorf tube to collect the labeled antibody after a 2 minute 1500×g spin. The labeled antibody is stored at 4° C. in the dark.

For the sandwich ELISA assay, on day 1, Antibody I is diluted to 4 µg/mL into 1×PBS (GIBCO® Life Technologies Cat #14190-144). 35 µL/well of this solution is applied to MesoScale Discovery MSD® Plates (Cat #L15XA-3). The plates are tapped to evenly coat the well. The plate is sealed and incubated overnight at room temperature. On day 2, the plates are washed three times using an automatic plate washer (Biotek ELx405) with 1×PBS with 0.05% TWEEN® 20 (20×PBS TWEEN® 20 Thermo Scientific Cat #28352). The plates are tapped dry on a paper towel. 100 µL of SUPERBLOCK® buffer (SUPERBLOCK® (T20) Thermo Scientific Cat #37536) are added to each well and shaken moderately for two hours at room temperature. Plates are washed three times and tapped dry as described above. 25 µL of SUPERBLOCK® buffer are added to all wells of the plates. Then 25 µL of four-fold serial dilutions (made in SUPERBLOCK® (T20)) starting at 500 ng/ml of either human INSL5 (Phoenix Pharmaceuticals Cat #035-70 made in DMSO) or mouse INSL5 (Phoenix Pharmaceuticals Cat #035-40 made in DMSO) are added to the respective wells in the plates. The plates are sealed and shaken moderately for 2 hours at room temperature. Plates are washed three times and tapped dry as described above. MSD® Sulfotag labeled antibody of Example 2 is diluted to 1 µg/mL (i.e. about 1000-fold) into 0.2× SUPERBLOCK® (T 20) buffer in 1×PBS/TWEEN® 0.05%. 25 µL of this solution is added to each well of the plate and incubated for 1 hour at room temperature. Plates are washed three times and tapped dry as described above. 150 µL of 1×MSD® Read buffer (MSD® Read Buffer (4×) Cat #R92TC-2) are added to each well and read on MSD® Sector plate reader. Signal is measured in Electrochemiluminscence units (ECLUs). TWEEN® is a US registered trademark of Croda Americas LLC. SUPERBLOCK® is a US registered trademark of Pierce Biotechnology, Inc. MSD® is a US registered trademark of Meso Scale Diagnostics, LLC. ZEBA® and GIBCO® are US registered trademarks of Life Technologies Corporation.

Statistical analysis of data: Data is imported from the Mesoscale Discovery Sector reader into MICROSOFT® EXCEL® and RAPHPAD PRISM® software (GraphPad Software, LLC; La Jolla, CA) to determine the approximate linear range for accurate INSL5 detection. Detection range approximates between 30 pg/mL and 100,000 pg/mL for both, human and mouse INSL5. MICROSOFT® and EXCEL® are US registered trademarks of Microsoft Corporation.

TABLE 5

Mouse and Human INSL5 Detection by Sandwich ELISA using Antibody I for Capture and Antibody II for Detection.

| Dilution No. | Human INSL5 | | Mouse INSL5 | |
|---|---|---|---|---|
| | Conc. (pg/mL) | ECLU | Conc. (pg/mL) | ECLU |
| 1 | 504800 | 218430 | 511700 | 244857 |
| 2 | 126200 | 238191 | 127925 | 248527 |
| 3 | 31550 | 93393 | 31981 | 124617 |
| 4 | 7887 | 19907 | 7995 | 21301 |
| 5 | 1972 | 4570 | 1999 | 6823 |
| 6 | 493 | 1231 | 450 | 1902 |
| 7 | 123 | 579 | 125 | 735 |
| 8 | 30.8 | 433 | 31.2 | 491 |
| 9 | 7.70 | 413 | 7.81 | 420 |
| 10 | 1.93 | 394 | 1.95 | 552 |
| 11 | 0.48 | 771 | 0.49 | 385 |
| Buffer only | 0 | 306 | 0 | 382 |

Amino Acid and Nucleotide Sequences

SEQ ID NO: 1: Human INSL5 A-chain
QDLQTLCCTDGCSMTDLSALC

SEQ ID NO: 2: Human INSL5 B-chain
KESVRLCGLEYIRTVIYICASSRW

SEQ ID NO: 3: Mouse INSL5 A-chain
RDLQALCCREGCSMKELSTLC

SEQ ID NO: 4: Mouse INSL5 B-chain
RQTVKLCGLDYVRTVIYICASSRW

SEQ ID NO: 5: HC of Antibody I
QSVEESGGRLVTPGTPLTLTCTASGFSLSSYDMGWVRQTPGEGLEWVGTISAGG
YTYYAHWAKGRFTISKSSTTVDLKMTSLTTEDTATYFCARERWNYDRSGGAGA
GYFDLWGPGTLVTVSSGQPKAPSVFPLAPCCGDTPSSTVTLGCLVKGYLPEPVTV
TWNSGTLTNGVRTFPSVRQSSGLYSLSSVVSVTSSSQPVTCNVAHPATNTKVDKT
VAPSTCSKPTCPPPELLGGPSVFIFPPKPKDTLMISRTPEVTCVVVDVSQDDPEVQF
TWYINNEQVRTARPPLREQQFNSTIRVVSTLPITHQDWLRGKEFKCKVHNKALPA
PIEKTISKARGQPLEPKVYTMGPPREELSSRSVSLTCMINGFYPSDISVEWEKNGK
AEDNYKTTPAVLDSDGSYFLYNKLSVPTSEWQRGDVFTCSVMHEALHNHYTQK
SISRSPGK SEQ ID NO: 6: HC DNA of Antibody I
CAGTCGGTGGAGGAGTCCGGGGGTCGCCTGGTCACGCCTGGGACACCCCTGA
CACTCACCTGCACAGCCTCTGGATTCTCCCTCAGTAGCTACGACATGGGCTGG
GTCCGCCAGACTCCAGGGGAGGGGCTGGAATGGGTCGGAACCATTAGTGCTG
GTGGTTACACGTACTACGCGCACTGGGCGAAAGGCCGATTCACCATCTCCAA
ATCCTCGACCACGGTGGATCTGAAAATGACCAGTCTGACGACCGAGGACACG -continued

| Amino Acid and Nucleotide Sequences |
|---|

```
GCCACCTATTTCTGTGCCAGAGAAAGATGGAATTACGATAGGTCTGGTGGTG
CTGGTGCTGGCTACTTTGACTTGTGGGGCCCAGGCACCCTGGTCACCGTCTCC
TCAGGGCAACCTAAGGCTCCATCAGTCTTTCCCCTCGCACCTTGCTGTGGTGA
CACGCCCTCATCCACGGTAACACTGGGCTGTCTTGTCAAAGGATACCTTCCGG
AGCCAGTCACAGTAACGTGGAACTCGGGAACATTGACAAACGGCGTAAGAAC
GTTTCCGTCGGTACGTCAAAGTTCAGGCCTCTACTCGCTCAGCTCCGTAGTAT
CGGTGACCTCATCCAGCCAGCCGGTGACTTGCAACGTGGCGCATCCCGCGAC
CAACACAAAAGTGGATAAGACCGTTGCACCCTCAACTTGCTCCAAGCCCACG
TGTCCCCCACCAGAGCTGCTCGGTGGGCCCTCGGTCTTTATCTTCCCTCCGAA
ACCCAAAGACACATTGATGATCTCTCGCACGCCGGAAGTCACGTGCGTGGTC
GTGGACGTCAGCCAAGATGACCCGGAAGTGCAATTCACCTGGTATATCAATA
ACGAACAGGTCAGAACGGCTCGGCCTCCTTTGCGAGAACAACAGTTCAATTC
CACTATCAGGGTTGTATCAACACTTCCCATCACACACCAAGATTGGCTTAGGG
GAAAGGAGTTTAAGTGTAAAGTGCACAATAAGGCTTTGCCAGCGCCTATTGA
GAAAACCATTTCCAAAGCCCGTGGGCAACCGCTTGAACCCAAAGTCTATACA
ATGGGGCCACCCAGAGAGGAACTGTCGAGCCGCTCCGTGTCACTGACTTGTA
TGATCAATGGGTTCTATCCGTCGGACATTTCGGTGGAATGGGAGAAGAATGG
AAAAGCAGAGGATAACTACAAAACTACGCCAGCCGTGTTGGACTCTGACGGG
TCATACTTTCTGTACAATAAGCTCTCTGTCCCCACGTCGGAATGGCAGAGGGG
AGATGTGTTTACTTGCTCGGTGATGCATGAGGCGCTCCATAATCACTATACCC
AGAAAAGCATCAGTCGAAGCCCTGGGAAA
```

SEQ ID NO: 7: LC of Antibody I
```
ADVVMTQTASPVSAAVGGTVTINCQASQSITSSYLSWYQQKPGQPPKLLIYPAAN
LASGVPSRFKGSGSGTQFTLTISGVQCDDAATYYCLYGYFSSSIDFAFGGGTEVV
VRGDPVAPTVLIFPPAADQVATGTVTIVCVANKYFPDVTVTWEVDGTTQTTGIEN
SKTPQNSADCTYNLSSTLTLTSTQYNSHKEYTCKVTQGTTSVVQSFNRGDC
```

SEQ ID NO: 8: LC DNA of Antibody I
```
GCCGATGTCGTGATGACCCAGACTGCATCCCCCGTGTCTGCAGCTGTGGGAG
GCACAGTCACCATCAATTGCCAGGCCAGTCAGAGTATTACTAGTAGCTACTTA
TCCTGGTATCAGCAGAAACCAGGGCAGCCTCCCAAGCTCCTGATCTATCCTGC
AGCCAATCTGGCATCTGGAGTCCCATCGCGGTTCAAAGGCAGTGGATCTGGG
ACACAGTTCACTCTCACCATCAGCGGCGTGCAGTGTGACGATGCTGCCACTTA
CTACTGTCTATACGGTTATTTTAGTTCTAGTATTGATTTTGCTTTCGGCGGAGG
GACCGAGGTGGTGGTCAGAGGTGATCCAGTTGCACCTACTGTCCTCATCTTCC
CACCAGCTGCTGATCAAGTCGCAACAGGTACTGTGACGATCGTGTGTGTCGC
GAACAAATACTTTCCCGACGTGACCGTGACGTGGGAAGTCGACGGAACAACC
CAGACGACCGGGATCGAAACTCAAAGACCCCGCAAAACTCGGCCGATTGCA
CATACAATTTGTCCTCTACGCTTACACTCACGTCGACGCAGTACAATAGTCAC
AAGGAGTATACATGCAAAGTTACTCAAGGAACTACGAGCGTGGTCCAGTCAT
TCAATAGAGGGGATTGT
```

SEQ ID NO: 9: VH of Antibody I
```
QSVEESGGRLVTPGTPLTLTCTASGFSLSSYDMGWVRQTPGEGLEWVGTISAGG
YTYYAHWAKGRFTISKSSTTVDLKMTSLTTEDTATYFCARERWNYDRSGGAGA
GYFDLWGPGTLVTVSS
```

SEQ ID NO: 10: HCDR 1 of Antibody I
```
TASGFSLSSYDMG
```

SEQ ID NO: 11: HCDR2 of Antibody I
```
TISAGGYTY
```

SEQ ID NO: 12: HCDR3 of Antibody I
```
ARERWNYDRSGGAGAGYFDL
```

SEQ ID NO: 13: VL of Antibody I
```
ADVVMTQTASPVSAAVGGTVTINCQASQSITSSYLSWYQQKPGQPPKLLIYPAAN
LASGVPSRFKGSGSGTQFTLTISGVQCDDAATYYCLYGYFSSSIDFAFGGGTEVV
VR
```

SEQ ID NO: 14: LCDR1 of Antibody I
```
QASQSITSSYLS
```

SEQ ID NO: 15: LCDR2 of Antibody I
```
YPAANLAS
```

SEQ ID NO: 16: LCDR3 of Antibody I
```
LYGYFSSSIDFA
```

SEQ ID NO: 17: HC of Antibody II
```
QSVEESGGGLVTPGGSLTLTCTVSGIDLTTYAMGWVRQAPGEGLEWIGIIGGGGR
TYYAAWAKGRFTISKTSTTVDLRITSPATEDTATYFCVRGGDFFDLWGPGTLVTV
SSGQPKAPSVFPLAPCCGDTPSSTVTLGCLVKGYLPEPVTVTWNSGTLTNGVRTF
PSVRQSSGLYSLSSVVSVTSSSQPVTCNVAHPATNTKVDKTVAPSTCSKPTCPPPE
LLGGPSVFIFPPKPKDTLMISRTPEVTCVVVDVSQDDPEVQFTWYINNEQVRTARP
```

-continued

---

Amino Acid and Nucleotide Sequences

---

PLREQQFNSTIRVVSTLPITHQDWLRGKEFKCKVHNKALPAPIEKTISKARGQPLE
PKVYTMGPPREELSSRSVSLTCMINGFYPSDISVEWEKNGKAEDNYKTTPAVLDS
DGSYFLYNKLSVPTSEWQRGDVFTCSVMHEALHNHYTQKSISRSPGK

SEQ ID NO: 18: HC DNA of Antibody II
CAGTCGGTGGAGGAGTCCGGAGGAGGCCTGGTAACGCCTGGAGGATCCCTGA
CACTCACCTGCACAGTCTCTGGAATCGACCTCACTACCTATGCAATGGGCTGG
GTCCGCCAGGCTCCAGGGGAGGGGCTGGAATGGATCGGAATTATTGGTGGTG
GTGGTCGAACATACTACGCGGCCTGGGCGAAAGGCCGCTTCACCATCTCCAA
AACCTCGACCACGGTGGATCTGAGAATCACCAGTCCGGCAACCGAGGACACG
GCCACCTATTTCTGTGTCAGAGGAGGAGACTTCTTTGACTTGTGGGGCCCAGG
CACCCTGGTCACCGTCTCCTCAGGGCAACCTAAGGCTCCATCAGTCTTTCCCC
TCGCACCTTGCTGTGGTGACACGCCCTCATCCACGGTAACACTGGGCTGTCTT
GTCAAAGGATACCTTCCGGAGCCAGTCACAGTAACGTGGAACTCGGGAACAT
TGACAAACGGCGTAAGAACGTTTCCGTCGGTACGTCAAAGTTCAGGCCTCTA
CTCGCTCAGCTCCGTAGTATCGGTGACCTCATCCAGCCAGCCGGTGACTTGCA
ACGTGGCGCATCCCGCGACCAACACAAAGTGGATAAGACCGTTGCACCCTC
AACTTGCTCCAAGCCCACGTGTCCCCCACCAGAGCTGCTCGGTGGGCCCTCGG
TCTTTATCTTCCCTCCGAAACCCAAAGACACATTGATGATCTCTCGCACGCCG
GAAGTCACGTGCGTGGTCGTGGACGTCAGCCAAGATGACCCGGAAGTGCAAT
TCACCTGGTATATCAATAACGAACAGGTCAGAACGGCTCGGCCTCCTTTGCGA
GAACAACAGTTCAATTCCACTATCAGGGTTGTATCAACACTTCCCATCACACA
CCAAGATTGGCTTAGGGGAAAGGAGTTTAAGTGTAAAGTGCACAATAAGGCT
TTGCCAGCGCCTATTGAGAAAACCATTTCCAAAGCCCGTGGGCAACCGCTTG
AACCCAAAGTCTATACAATGGGGCCACCCAGAGAGGAACTGTCGAGCCGCTC
CGTGTCACTGACTTGTATGATCAATGGGTTCTATCCGTCGGACATTTCGGTGG
AATGGGAGAAGAATGGAAAAGCAGAGGATAACTACAAAACTACGCCAGCCG
TGTTGGACTCTGACGGGTCATACTTTCTGTACAATAAGCTCTCTGTCCCCACG
TCGGAATGGCAGAGGGGAGATGTGTTTACTTGCTCGGTGATGCATGAGGCGC
TCCATAATCACTATACCCAGAAAAGCATCAGTCGAAGCCCTGGGAAA SEQ ID NO: 19: LC of Antibody II
AQVLTQTPASVSAAVGGTVTIKCQASEDISKYLSWYQQKPGQRPKLLIYYVSNLE
FGVPSRFKGSGSGTEYTLTISDLECDDAATYYCHQGYTGVNVENVFGGGTEVVV
RGDPVAPTVLIFPPAADQVATGTVTIVCVANKYFPDVTVTWEVDGTTQTTGIENS
KTPQNSADCTYNLSSTLTLTSTQYNSHKEYTCKVTQGTTSVVQSFNRGDC SEQ ID NO: 20: LC DNA of Antibody II
GCTCAAGTGCTGACCCAGACTCCAGCCTCCGTGTCTGCAGCTGTGGGAGGCA
CAGTCACCATCAAGTGCCAGGCCAGTGAGGATATTAGCAAGTACTTATCCTG
GTATCAGCAGAAACCAGGGCAGCGCCCCAAACTCCTGATCTATTATGTATCC
AATCTGGAATTTGGGGTCCCATCGCGGTTCAAAGGCAGTGGATCTGGGACAG
AGTACACTCTCACCATCAGCGACCTGGAGTGTGACGATGCTGCCACTTACTAC
TGTCACCAGGGTTATACCGGTGTTAATGTTGAAAATGTTTTCGGCGGAGGGAC
CGAGGTGGTGGTCAGAGGTGATCCAGTTGCACCTACTGTCCTCATCTTCCCAC
CAGCTGCTGATCAAGTCGCAACAGGTACTGTGACGATCGTGTGTGTCGCGAA
CAAATACTTTCCCGACGTGACCGTGACGTGGGAAGTCGACGGAACAACCCAG
ACGACCGGGATCGAAAACTCAAAGACCCCGCAAAACTCGGCCGATTGCACAT
ACAATTTGTCCTCTACGCTTACACTCACGTCGACGCAGTACAATAGTCACAAG
GAGTATACATGCAAAGTTACTCAAGGAACTACGAGCGTGGTCCAGTCATTCA
ATAGAGGGGATTGT SEQ ID NO: 21: VH of Antibody II
QSVEESGGGLVTPGGSLTLTCTVSGIDLTTYAMGWVRQAPGEGLEWIGIIGGGGR
TYYAAWAKGRFTISKTSTTVDLRITSPATEDTATYFCVRGGDFFDLWGPGTLVTV
SS SEQ ID NO: 22: HCDR1 of Antibody II
TVSGIDLTTYAMG SEQ ID NO: 23: HCDR2 of Antibody II
IIGGGGRTY SEQ ID NO: 24: HCDR3 of Antibody II
VRGGDFFDL SEQ ID NO: 25: VL of Antibody II
AQVLTQTPASVSAAVGGTVTIKCQASEDISKYLSWYQQKPGQRPKLLIYYVSNLE
FGVPSRFKGSGSGTEYTLTISDLECDDAATYYCHQGYTGVNVENVFGGGTEVVV
R SEQ ID NO: 26 LCDR1 of Antibody II
QASEDISKYLS SEQ ID NO: 27 LCDR2 of Antibody II
YYVSNLEF -continued ---
Amino Acid and Nucleotide Sequences
---

SEQ ID NO: 28 LCDR3 of Antibody II
HQGYTGVNVENV

SEQ ID NO: 29 Signal peptide
METDTLLLWVLLLWVPGSTG

---

We claim:

1. An antibody that binds INSL5, wherein the antibody comprises a heavy chain variable region (VH) and a light chain variable region (VL), wherein the VH comprises heavy chain complementarity determining regions (HCDR) HCDR1, HCDR2, and HCDR3, and the VL comprises light chain complementarity determining regions (LCDR) LCDR1, LCDR2, and LCDR3, wherein

```
the HCDR1 comprises
                                (SEQ ID NO: 10)
TASGFSLSSYDMG, the HCDR2 comprises
                                (SEQ ID NO: 11)
TISAGGYTY, the HCDR3 comprises
                                (SEQ ID NO: 12)
ARERWNYDRSGGAGAGYFDL, the LCDR1 comprises
                                (SEQ ID NO: 14)
QASQSITSSYLS,
```

```
                    -continued
the LCDR2 comprises
                                (SEQ ID NO: 15)
YPAANLAS,
and the LCDR3 comprises
                                (SEQ ID NO: 16)
LYGYFSSSIDFA.
```

2. The antibody of claim 1, wherein the VH comprises SEQ ID NO:9 and the VL comprises SEQ ID NO:13.

3. The antibody of claim 1, wherein the antibody comprises a heavy chain (HC) comprising SEQ ID NO:5 and a light chain (LC) comprising SEQ ID NO:7.

4. The antibody of claim 1, wherein the antibody comprises a heavy chain (HC) comprising amino acids 2-446 of SEQ ID NO:5, and a light chain (LC) comprising SEQ ID NO:7.

5. The antibody of claim 1, wherein the antibody comprises a HC consisting of SEQ ID NO:5 and a LC consisting of SEQ ID NO:7.

6. The antibody of claim 1, wherein the antibody binds to human INSL5.

7. The antibody of claim 1, wherein the antibody binds to mouse INSL5.

8. A nucleic acid comprising a sequence encoding SEQ ID NO:5 or SEQ ID NO:7.

9. A composition comprising a first vector comprising a nucleic acid encoding the protein of SEQ ID NO:5 and a second vector comprising a nucleic acid encoding the protein of SEQ ID NO:7.

10. A cell comprising:
(a) a first vector comprising a nucleic acid encoding a protein of SEQ ID NO:5 and a second vector comprising a nucleic acid encoding a protein of SEQ ID NO:7; or
(b) a vector comprising a first nucleic acid encoding a protein of SEQ ID NO:5 and a second nucleic acid encoding a protein of SEQ ID NO: 7.

11. An antibody that binds INSL5, wherein the antibody comprises a VH and a VL, wherein the VH comprises HCDR1, HCDR2, and HCDR3, and the VL comprises LCDR1, LCDR2, and LCDR3, wherein

```
the HCDR1 comprises
                              (SEQ ID NO: 22)
TVSGIDLTTYAMG, the HCDR2 comprises
                              (SEQ ID NO: 23)
IIGGGGRTY, the HCDR3 comprises
                              (SEQ ID NO: 24)
VRGGDFFDL, the LCDR1 comprises
                              (SEQ ID NO: 26)
QASEDISKYLS, the LCDR2 comprises
                              (SEQ ID NO: 27)
YYVSNLEF,
```

```
-continued
and the LCDR3 comprises
                              (SEQ ID NO: 28)
HQGYTGVNVENV.
```

12. The antibody of claim 11, wherein the VH comprises SEQ ID NO:21 and the VL comprises SEQ ID NO:25.

13. The antibody of claim 11, wherein the antibody comprises a heavy chain (HC) comprising SEQ ID NO:17 and a light chain (LC) comprising SEQ ID NO:19.

14. The antibody of claim 11, wherein the antibody comprises a heavy chain (HC) comprising amino acids 2-435 of SEQ ID NO:17, and a light chain (LC) comprising SEQ ID NO:19.

15. The antibody of claim 11, wherein the antibody comprises a HC consisting of SEQ ID NO: 17 and a LC consisting of SEQ ID NO: 19.

16. The antibody of claim 11 wherein the antibody binds to human INSL5.

17. The antibody of claim 11 wherein the antibody binds to mouse INSL5.

18. A nucleic acid comprising a sequence encoding SEQ ID NO:17 or SEQ ID NO:19.

19. A composition comprising a first vector comprising a nucleic acid encoding a protein of SEQ ID NO:17 and a second vector comprising a nucleic acid encoding a protein of SEQ ID NO:19.

20. A cell comprising:
(a) a first vector comprising a nucleic acid encoding a protein of SEQ ID NO:17 and a second vector comprising a nucleic acid encoding a protein of SEQ ID NO:19; or
(b) a vector comprising a first nucleic acid encoding a protein of SEQ ID NO:17 and a second nucleic acid encoding a protein of SEQ ID NO:19.

* * * * *